(12) United States Patent
Vernengo et al.

(10) Patent No.: US 9,446,167 B2
(45) Date of Patent: Sep. 20, 2016

(54) SELF-ASSEMBLING BIOMIMETIC HYDROGELS HAVING BIOADHESIVE PROPERTIES

(71) Applicant: Rowan University, Glassboro, NJ (US)

(72) Inventors: Andrea Jennifer Vernengo, Swedesboro, NJ (US); Jennifer Kadlowec, Haddon Township, NJ (US); Pamela Kubinski, Jackson, NJ (US); Thomas N. Tulenko, Ambler, PA (US); Cristina Iftode, Princeton, NJ (US); Bryan Johnson, Philadelphia, PA (US); Craig Wiltsey, Mantua, NJ (US)

( * ) Notice: Subject to any disclaimer, the term of this patent is extended or adjusted under 35 U.S.C. 154(b) by 0 days.

(21) Appl. No.: 15/041,170

(22) Filed: Feb. 11, 2016

(65) Prior Publication Data
US 2016/0158406 A1 Jun. 9, 2016

Related U.S. Application Data

(63) Continuation of application No. 13/652,408, filed on Oct. 15, 2012, now Pat. No. 9,295,761.

(60) Provisional application No. 61/546,923, filed on Oct. 13, 2011.

(51) Int. Cl.
| | |
|---|---|
| *A61K 9/00* | (2006.01) |
| *A61L 24/04* | (2006.01) |
| *A61L 24/00* | (2006.01) |
| *A61F 2/00* | (2006.01) |

(52) U.S. Cl.
CPC ............ *A61L 24/043* (2013.01); *A61F 2/0063* (2013.01); *A61L 24/0015* (2013.01); *A61L 24/0031* (2013.01); *A61F 2002/0068* (2013.01); *A61L 2300/252* (2013.01); *A61L 2300/412* (2013.01); *A61L 2430/38* (2013.01)

(58) Field of Classification Search
CPC .................................................. C08G 2210/00
See application file for complete search history.

*Primary Examiner* — Paul Dickinson
(74) *Attorney, Agent, or Firm* — Fox Rothschild LLP; Shahnam Sharareh; Robert N. Henrie, II

(57) ABSTRACT

The disclosure relates to a composition that is liquid at a temperature below the body temperature of a mammal and that solidifies at or above the body temperature of the mammal. The composition includes a thermally-desolubilizable polymer interspersed with a polymeric component of extracellular matrix and an encapsulated form of an amine compound (preferably an aminated component of extracellular matrix) that is de-encapsulated in the body of the mammal. The polymeric component is able to form covalent bonds with amine moieties in the aminated component, in one or more tissues in the body of the mammal, or both. Upon injection of a liquid suspension of these components into the body of the mammal, the thermally-desolubilizable polymer condenses, entrapping the polymeric component. The polymeric component binds covalently with a tissue in the body, and the aminated component end-caps the remaining reactive moieties of the polymeric component, forming a matrix at the site of injection. The disclosure also relates to uses of such compositions for forming a matrix on or within the body of a mammal. The compositions have a variety of uses, such as bioadhesives, as sealants for ruptured tissues, as drug or imaging agent depots, or as mechanical cushions.

19 Claims, 6 Drawing Sheets

SELF-ASSEMBLING BIOMIMETIC HYDROGELS HAVING BIOADHESIVE PROPERTIES

CROSS-REFERENCES TO RELATED APPLICATIONS

The present application is a continuation of U.S. patent application Ser. No. 13/652,408, filed Oct. 15, 2012, and is entitled to priority pursuant to 35 U.S.C. §119(e) to U.S. provisional patent application 61/546,923, which was filed on 13 Oct. 2011.

BACKGROUND OF THE DISCLOSURE

The disclosure relates generally to the fields of tissue engineering and implantation.

Tissue engineering is a multidisciplinary field, in which practitioners aim to repair or regenerate lost or damaged tissues and organs in the body. A goal of tissue engineering workers is to design biomimetic scaffolds, which are three-dimensional engineered biomaterials that reproduce the mechanical and biochemical properties of natural tissue. Such materials should have desirable biological properties such that the biomaterials will, after implantation or application to a subject, become populated with the subject's cells (e.g., stem cells) which can promote formation of new extracellular matrix (ECM) and establishment of cell populations similar to or indistinguishable from those of tissue(s) or organ(s) that the materials are intended to resemble. The scaffolding material can remain in place indefinitely, and is preferably resorbable, such that it gradually disappears over time (e.g., through consumption of the scaffolding material by cells or by chemical decomposition over time).

Others have recognized the desirability of generating materials for use as bioscaffolds and/or bioadhesives. The following represent examples of such.

Strehin et al. have developed a chondroitin sulfate-polyethylene glycol (CS-PEG) adhesive hydrogel material for use as a bioscaffold (Strehin et al., 2010, Biomaterials 31:2788-2797). Carboxyl groups on CS chains were functionalized to yield CS-N-hydroxysuccinimide (CS-NHS). The CS-NHS molecule can react with primary amines to form amide bonds. However, long-term cell viability and differentiation within the matrix in the presence of reactive NHS groups was not reported and may be undesirable.

Wang et al. developed another tissue adhesive for cartilage regeneration based on an aldehyde-functionalized CS (Wang et al., 2007, Nature Mat. 6:385-392). Adhesion to a cartilage interface was demonstrated in vivo. However, only the survival of cells at the hydrogel-tissue interface, not within the matrix, was reported. Furthermore, injectability of such a system requires the implantation of methacrylate-functionalized CS macromers followed by in situ crosslinking. Potential problems with such in situ reactions include leaking of unreacted macromers into the physiological environment and heat generation.

Burke et al. developed a PEG-based system was developed that allows temperature-mediated release of sodium periodate, which is an oxidizing agent that converts the PEG chains into dialdehydes. Release of periodate induces attachment to surrounding tissues following implantation (Burke et al., 2007, Biomed. Mat. 2:203-210). While the idea of temperature sensitive release is appealing, the prospect of releasing sodium periodate, a potential toxic compound, in situ may limit the practical applicability of such compositions in ethical practice involving human or other subjects.

US patent application publication number 2002/0068087 discloses a bioadhesive for mucosa that is susceptible to enzymatic cleavage. The bioadhesive polymer described therein is synthesized by polymerization of vinyl monomers and crosslinked by a molecule that is degradable in vivo in mammals. This material is not injectable. US patent application publication number 2002/0092776 discloses a mucoadhesive material that exhibits thermally-triggered viscosification. The material is composed of a blend of poloxamers (polyoxyethylene-polyoxypropylene-polyoxyethylene block copolymers) and polyacrylic acid. The material is disclosed to be useful for solubilization and local delivery of drugs. US patent application publication number 2006/0258788 discloses a bioadhesive polymer useful for coating biomedical electrodes. The disclosed material is composed of interpenetrating networks of two polymers, one containing carboxylic acids. Tissue adhesion by each of these three materials occurs primarily by way of hydrogen bonding. As a result, adhesion of these materials to tissue is relatively weak—likely too weak for many or most practical uses for implantation in animal subjects, especially in load-bearing situations (e.g., for implantation within or in place of intervertebral disc material in a human).

US patent application publication number 2008/0076852 discloses copolymers of poly(N-isopropylacrylamide) (and PEG copolymers thereof) with an amine-containing polymeric component. The copolymer is thermally responsive. Tissue adhesion of the copolymer occurs following injection of a dialdehyde (e.g., glutaraldehyde) into the gel. US patent application publication number 2010/0286786 discloses a multi-component system containing 1) an amine-containing polymer (e.g., a polyethylene imine), 2) a hydrophilic polymer (e.g., a PEG or a poly(vinyl alcohol)), and 3) a dialdehyde (e.g., glutaraldehyde). Owing to the potential for significant toxicity, the materials in these applications may be inappropriate for tissue engineering applications.

Significant shortcoming of some previously known scaffolding materials include undesirable toxicity and post-implantation/-application dislocation of the material from its original site. Such dislocation can contribute to failure of the material and its resident cells to integrate with surrounding host tissue, thereby inhibiting or preventing reestablishment of normal, hybrid, or replacement tissue at the desired body location. Such shortcomings could be avoided if the scaffolding material could be better secured at the site of application or implantation. The present disclosure describes materials which do not exhibit these shortcomings, at least to the degree they are exhibited by many previously-known materials.

Bioadhesive polymers are natural or synthetic materials that have been traditionally used for soft tissue repair, such wound closure, achieving hemostasis after a surgical procedure, or fistula repair. Bioadhesive materials can supplement the use of sutures or replace them altogether.

Fibrin adhesives are bioadhesives that act as a hemostatic plug by mimicking the last stage of blood clotting. The clot is resorbed within days or weeks allowing healing to occur at the site of adhesion. Because they are natural materials, fibrin sealants are completely biocompatible (Spotnitz et al., 2005, J. Long-Term Effects Med. Implants 15:245-270). However, the main drawback to this class of adhesives is a low cohesive strength (Siedentop et al., 1998, Laryngoscope 98:731-733; Sierra et al., 1992, J. Appl. Biomater. 3:147-151).

Another major group of bioadhesives known for its improved strength over fibrin is based on glutaraldehyde. Glutaraldehyde is an aliphatic organic molecule with aldehyde groups at each end. The di-aldehydes are able to react readily with the amines on proteins of the tissue extracellular matrix, via a Schiff's base reaction (Guibal et al., 1999, Int. J. Biol. Macromol. 24:49-59), resulting in covalent crosslinks. Despite its high adhesive strength, inflammatory responses have been associated with glutaraldehyde application and have been ascribed to its cytotoxicity (Chang et al., 2002, Biomaterials 23:2447-2457; Fürst et al., 2005, Ann. Thorac. Surg. 79:1522-1529).

An unmet need exists at the intersection of bioadhesives and tissue engineering for a polymer that can form a strong bond with tissue and also support long-term cell survival. The subject matter disclosed herein addresses this need.

BRIEF SUMMARY OF THE DISCLOSURE

The disclosure relates to a liquid composition for forming a solidified matrix within the body of a mammal (e.g., a human). The composition includes an aqueous solvent having suspended therein:

a) a biocompatible thermally-desolubilizable (TD) polymer that exists in an extended form below a critical solution temperature (CST) that is lower than the normal body temperature of the mammal and in a condensed form at or above the CST;

b) an aminated component of a mammalian extracellular matrix (ECM), in a releasable encapsulated form, wherein the aminated component is releasable from the encapsulated form within the body of the mammal; and c) a polymeric component of a mammalian ECM, the polymeric component bearing functional moieties capable of forming covalent bonds with amine moieties.

When the composition is injected into the body of the mammal, the polymer is transformed from its extended form to its condensed form, the aminated component is released from its encapsulated form, and the polymeric component binds with the aminated component, thereby forming the matrix.

The TD polymer can be any of a number of such polymers, such as one is selected from the group consisting of poly(ethylene oxides) (PEOs), poly(propylene oxides) (PPOs), copolymers of PEO and poly(lactic acid) (PLA), poly(n-isopropyl acrylamides) (PNIPAAms), mixtures of the foregoing, and copolymers of the foregoing. The TD polymer can also be covalently linked with an ECM polymer (e.g., the same polymer as the polymeric component).

The aminated component can, for example, be a synthetic analog of a mammalian ECM component or an aminated component is isolated from mammalian (e.g., substantially purified human) ECM. The aminated component can be encapsulated in a thermally-releasable or a diffusionally-releasible manner, such as within lipid vesicles or dissolvable polymeric mircoparticles. Examples of suitable aminated components include chondroitins, hyaluronates, keratins, alginates, celluloses, gums, and dextrans.

The polymeric component can be functionalized to render it capable of covalently bonding with amine moieties in the mammal's tissue. Example of suitable polymeric components include chondroitins, hyaluronates, keratins, alginates, celluloses, gums, and dextrans.

In addition to these components, the composition can further include a bioactive agent dissolved or suspended in the solvent. Examples of suitable bioactive agents include mammalian cells, pharmaceutical agents, imaging agents, and radionuclides.

The disclosure also relates to a kit for making the liquid composition. The kit includes:

a) a biocompatible thermally-desolubilizable polymer, in a dehydrated form, wherein the polymer is one that exists in an extended form in aqueous suspension below a CST that is lower than the normal body temperature of the mammal and in a condensed form in aqueous suspension at or above the CST;

b) an aminated component of a mammalian extracellular matrix, in a releasable encapsulated form, wherein the aminated component is releasable from the encapsulated form within the body of the mammal; and c) a polymeric component of a mammalian extracellular matrix in a dehydrated form, the polymeric component bearing functional moieties capable of forming covalent bonds with the aminated component when the polymeric component is in a hydrated form.

When components a), b), and c) are suspended in an aqueous solvent having a temperature below the CST and the resulting suspension is injected into the body of the mammal, the polymer is transformed from its hydrated form to its condensed form, the aminated component is released from its encapsulated form, and the polymeric component binds with the aminated component, thereby forming the matrix.

In another aspect, the disclosure relates to a method of forming a solidified matrix fixed within the body of a mammal. The method includes the steps of:

1) Suspending in an aqueous solvent:

a) a biocompatible thermally-desolubilizable polymer, wherein the polymer exists in an extended form below a critical solution temperature (CST) that is lower than the normal body temperature of the mammal and in a condensed form at or above the CST;

b) an aminated component of a mammalian extracellular matrix, in a releasable encapsulated form, wherein the aminated component is releasable from the encapsulated form within the body of the mammal; and c) a polymeric component of a mammalian extracellular matrix, the polymeric component bearing functional moieties capable of forming covalent bonds with both the aminated component and amine moieties at a tissue in the body of the mammal, and 2) Injecting the suspension into the body of the mammal at a desired location for the matrix.

Following such injection, the polymer is transformed from its extended form to its condensed form, the aminated component is released from its encapsulated form, and the polymeric component binds with both the tissue and the aminated component, thereby forming the matrix fixed at the location.

BRIEF SUMMARY OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 1 consists of FIGS. 1A and 1B and is a pair of diagrams depicting the compositions described herein, which include (in the embodiment shown in this figure) mesenchymal stem cells (MSC), lipid vesicles (L) containing an aminated component of a mammalian extracellular matrix in a releasable form (R), PNIPAAm polymer chains (P) cross-linked with chondroitin sulfate chains (CS) having bioadhesive sites (B) capable of binding with MSCs, P, and R. In FIG. 1B, the PNIPAAm polymer chains (P) have been desolubilized, CS chains (CS) linked to the P chains link the P chains into a hydrogel matrix, and MSCs are bound to the matrix by way of the bioadhesive sites (B in FIG. 1A); aminated components of extracellular matrix (R) bind with non-reacted bioadhesive sites (B in FIG. 1A).

DETAILED DESCRIPTION

Figure 1A:
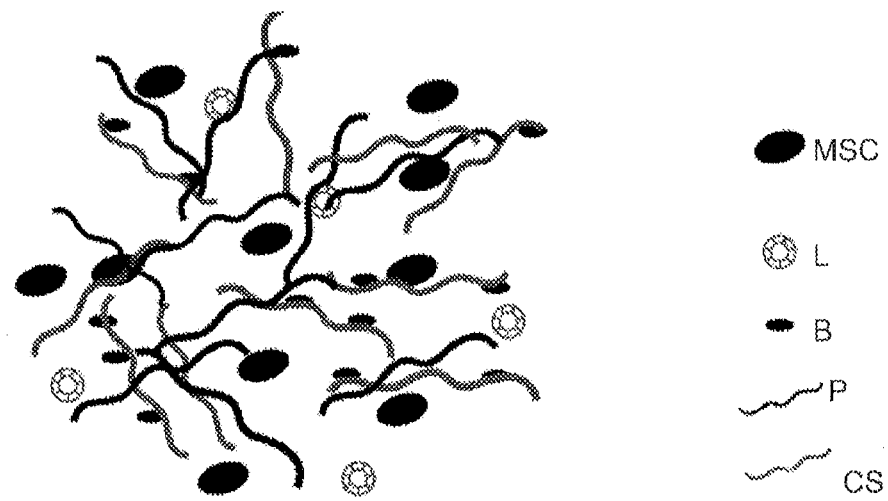
FIG. 1A depicts the composition at a temperature below the critical solution temperature of the PNIPAAm polymer chains; all components are suspended in a solvent.
Figure 1B:
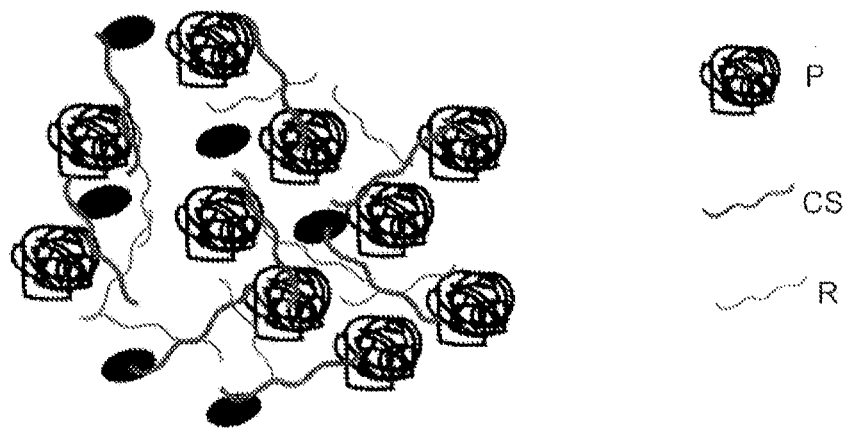
FIG. 1B depicts the composition at a temperature above the critical solution temperature of the PNIPAAm polymer chains.

The subject matter disclosed herein relates to bioadhesive materials that exhibit relatively low toxicity and significant biocompatibility, and which are useful as bioscaffolding materials for initiating, facilitating, and propagating establishment, growth, and interconnection of cells within the material. In particular, the subject matter relates to a multi-component hydrogel system that covalently adhere to surrounding tissue following application, injection, or implantation, but which remain in a more conveniently handled liquid form prior to such application, injection, or implantation.

The compositions include three primary components: 1) thermally-desolubilizable polymer (TDP) chains interspersed with 2) a polymeric component of extracellular matrix (ECM), and 3) aminated ECM components (AECMC) encapsulated in a thermally-releasible form. The polymeric component bears chemical moieties that are capable of forming covalent bonds between the polymeric component and an amine moiety of another compound when the polymeric component and the other compound are brought into sufficiently close proximity to react with one another. Thus, the polymeric component can form covalent bonds with proteins and other amine-containing compounds present at tissue surfaces, as well as with the AECMC of the composition. TDP chains interspersed with the polymeric component can condense upon thermal transition, fixing the matrix to the polymeric components linked with tissue surfaces, thereby fixing the matrix in place. The AECMC and other components within the matrix can also be fixed at the tissue site. If not linked to the matrix, the AECMC and other components can move or diffuse from the matrix.

The TDP chains also have an ECM polymer (e.g., one or more of chondroitin polymers, hyaluronate polymers, keratin polymers, alginates, celluloses, guar gum, dextrans, or other carbohydrate and/or amino acid polymers) linked (e.g., covalently) thereto (e.g., at one or both ends of the TDP chains or at one or more positions along the length of the TDP chains). In a preferred embodiment, the TDP chains are covalently linked with an ECM polymer that is the same polymer as the polymeric component of ECM described herein. When the same ECM polymer is used, the ECM polymer linked to the TDP chains can, but need not, also bear the moieties that enable the polymeric component to bind with AECMC of the composition and with tissue sites. Such hybrid molecules can improve the biocompatibility, hydrophilicity, or other properties of TDP chains, as well as their ability to intermix with the polymeric component of ECM. Throughout this disclosure, the abbreviation TDP-PC is used to refer collectively to 'naked' TDP chains (i.e., those not covalently linked with an ECM polymer) and to TDP chains covalently linked with an ECM polymer.

The composition is used by suspending TDP-PC and the AECMC in an aqueous fluid (e.g., water, a buffer, saline, or a body fluid extracted from a mammal). The AECMC are encapsulated in a material that substantially prevents contact between the TDP-PC and the AECMC, so that the AECMC are not covalently linked with the TDP-PC in the suspension (which would otherwise lead to undesirable gelling of the suspension). The material used to encapsulate the AECMC exhibits barrier properties, such that the AECMC substantially do not contact the aqueous fluid under conditions at which the suspension is prepared and handled, but the AECMC contacts the aqueous fluid following delivery.

In one embodiment, the AECMC are compartmentalized within temperature-sensitive materials, such as lipid vesicles. The temperature of the suspension is maintained below the CST of the thermally-desolubilizable polymer chains, which is not greater than the body temperature of the mammal to which the suspension will be delivered. Upon delivery, the materials undergo a thermal transformation to the body temperature of the mammal that permits delivery (gradual or immediate) of AECMC from the inside of their compartment to the matrix, where they can react with the amine-reactive moieties of the polymeric component and/or diffuse from the matrix into the animal's tissues. Such release and reaction with the polymeric component can "end-cap" the reactive moities of the polymeric component and thereby prevent undesirable reactions (e.g., capture of cells or debris) involving those moieties.

In another embodiment, the AECMC are compartmentalized within vesicles or particles from which they are released by simple diffusion, such as microparticulates of a polymer matrix (optionally coated with a dissolvable or degradable coating) from which AECMC diffuse. In these embodiments, the vesicles or particles containing the AECMC can be combined with the other components of the suspension relatively soon before delivery of the suspension to a mammal, so that extensive diffusion of AECMC within the suspension will not occur prior to delivery of the suspension (i.e., and the AECMC will not 'end-cap' all of the reactive moieties of the polymeric component before they have an opportunity to react with tissue sites in the mammal).

When the suspension is delivered to a site on, within, or in thermal communication with the body of a mammal, the suspension warms. Encapsulated AECMC diffuses into the millieu (upon warming of the suspension, if temperature-sensitive encapsulation is used; by simple diffusion if a diffusion/dissolution-mediated carrier is used). Because the CST of the TDP-PC is not greater than the body temperature of the mammal, warming of the suspension also causes desolubilization of TDP-PC and entrapment of the interspersed polymeric component within the TDP-PC. Desolubilization of the TDP-PC also leads to their compaction within the aqueous millieu surrounding them, thereby securing the entangled polymeric component as well. The polymeric component of ECM is able to form covalent bonds with AECMC in the millieu, with tissue of the mammal, and with any amine moieties of TDP-PC. Cross-linking and compaction can occur sequentially or substantially simultaneously (e.g., by selecting AECMC encapsulating materials having a thermal transition temperature greater than/less than or substantially equal to the CST or by using encapsulating materials having a selected rate of diffusion or dissolution). Thus, one can generate a compacted, cross-linked hydrogel structure having a variety of mechanical properties. That is, one can generate at the delivery site a hydrogel matrix that is cross-linked-and-then-compacted, a hydrogel matrix in which compacted TDP-PC is cross-linked after compaction, or a hydrogel matrix that simultaneously compacts and cross-links. Selection among this spectrum of alternatives will depend on the desired properties of the hydrogel matrix and is within the ken of an ordinarily-skilled artisan in this field.

The composition can include a variety of bioactive agents in addition to the three components described above. For example, the composition can include one or more of a mammalian cell, a pharmaceutical agent, an imaging agent, another component of ECM, another hydrogel, and a radionuclide. Other agents (whether bioactive or not) can also be incorporated, so long as they do not significantly alter the functionality of the three components described above.

In addition to the three components of the suspension, the composition can include one or more components of another hydrogel (or multiple other hydrogels). Such hydrogels can interpenetrate the hydrogel(s) formed by the TDP-PC and polymeric components of the composition described herein. If another hydrogel is present in an interpenetrating network with the hydrogel(s) formed by the components of the composition described above at the time the temperature of the composition rises above the CST, then the other hydrogel will be trapped within them as the TDP-PC and polymeric component compacts.

An example of the bioadhesive compositions and their components is depicted in FIG. 1. In the embodiment shown in this figure, thermally-desolubilizable polymer chains (P in FIG. 1) are interspersed with chondroitin sulfate (CS) chains having amine-reactive moieties (B). FIG. 1A depicts the composition at a temperature lower than the critical solution temperature (CST) of the thermally-desolubilizable polymer chains.

In FIG. 1A, P and the CS chains are suspended in an aqueous solution, as are cells (MSCs in FIG. 1) and lipid vesicles (L) containing aminated components of mammalian extracellular matrix (ECM). FIG. 1B depicts the composition at a temperature that is higher than the CST of the thermally-desolubilizable polymer chains (P) and at which aminated ECM components (R) can be released from lipid vesicles (L).

In FIG. 1B, the thermally-desolubilizable polymer chains (P) have undergone a thermally-induces phase change from the open, hydrated, soluble conformation shown in FIG. 1A to a more compact, dehydrated, insoluble conformation, depicted in FIG. 1B as a coiled line. At the temperature of the composition in FIG. 1B, aminated ECM components (R) are released from the encapsulating lipid vesicles (L) shown in FIG. 1A. The P contracts and entraps CS chains. Because the CS chains include moieties (B) that are able to form covalent bonds with cells and with aminated ECM components, the thermally-desolubilizable polymer chains (P) are cross-linked with one another by way of CS chains that have formed covalent bonds with cells or components (which are also covalently bound to other entangled P-CS units). As a result, the composition and its components becomes cross-linked as a three-dimensional hydrogel. If the composition shown in FIG. 1B contacts a mammalian tissue surface, the CS chains can form covalent bonds with amine moieties at the tissue surface, thereby covalently anchoring the hydrogel to the surface.

Definitions

As used herein, each of the following terms has the meaning associated with it in this section.

A material is "biocompatible" if the material does not induce a medically-significant adverse pathological event upon implantation of the material at a location in or on the body of a mammal.

A "thermally-desolubilizable" polymer is polymer that will undergo a phase transition from an extended, more soluble (i.e., more suspendable) form to a compacted, less soluble (i.e., less suspendable; or even essentially completely insoluble) form when the temperature of an aqueous suspension of the polymer is raised above a critical solution temperature that is a characteristic of the polymer.

An "aminated" component of mammalian ECM is a constituent part of such a matrix that either includes an amine moiety in its naturally-occurring state or has been chemically modified to include an amine moiety.

A composition is "bioactive" if it exhibits utility when present on or at a body location of a mammal. Such utility can be pharmacological activity, utility as a marker or indicator (e.g., an imaging contrast agent), biomechanical utility (e.g., providing a cushion between abutting bones or sealing a body cavity), for example.

The Thermally-Desolubilizable (TD) Polymer

The TD polymer component may be substantially any biocompatible polymer that undergoes a thermal phase transition from a hydrated form that exists as a suspension to a generally dehydrated (or less-hydrated) form that exists as a gelatinized matrix (e.g., a hydrogel) as the temperature of the TD polymer passes below a critical solution temperature (CST) that is, generally speaking, an inherent property of the TD polymer. Examples of known TD polymers include copolymers of poly(ethylene oxide) (PEO) and poly(propylene oxide) (PPO), copolymers of PEO and poly (lactic acid) (PLA). A preferred TD polymer is poly(n-isopropyl acrylamide) (PNIPAAm) or one of its copolymers, such as copolymers of PNIPAAm and extracellular matrix polymers such as chondroitin sulfate (CS). Further examples of suitable TD polymers are described, for example, in U.S. patent application Ser. No. 10/837,082.

The TD Polymer is preferably the thermally sensitive polymer PNIPAAm. Below its lower critical solution temperature (LCST=32° C.), PNIPAAm forms a miscible suspension with water in which the PNIPAAm exists in an extended form. Above the LCST, it becomes hydrophobic, so the polymer and water separate, forming a compact gel (i.e., it assumes a condensed form). Aqueous suspensions of PNIPAAm can be implanted non-invasively through a small gauge needle and solidify in situ when injected into a human body.

The CST of the TD polymer used in the compositions described herein is preferably in the range 4° C. to 37° C., preferably in the range 20° C. to 35° C., and even more preferably in the range 25° C. to 33° C. These CST values are preferred so that the composition can be prepared and handled in a liquid form prior to injection into or application to a body site and so that the composition will solidify (i.e., form a hydrogel) once it has been delivered to a subject body site (i.e., so that a solid matrix will form as the composition warms to the subject's body temperature).

In a preferred form, the TD polymer has linked thereto at least one mammalian ECM polymer. Suitable ECM polymers are substantially the same as those which are suitable for use as the polymeric component and include polymers such as chondroitins (e.g., chondroitin sulfate, CS), gelatins, keratins, hyaluronates, alginates, celluloses, guar and other gums, and dextrins. The ECM polymer can exhibit desirable properties such as enzymatic degradability, anti-inflammatory activity, compatibility with the polymeric component, and water and nutrient absorption compatibility.

The Polymeric Component of ECM

The composition described herein includes a polymeric component of a mammalian ECM. The polymeric component is modified such that it includes functional chemical groups that can form covalent bonds with one or both of components of the mammal's tissue(s) at the site of application and the aminated ECM component that is part of the composition described herein. By way of example, a polymeric component functionalized with aldehyde groups can react with amines, via a Schiff's base reaction, thus rendering the polymeric component bioadhesive upon contact with amines of extracellular matrix proteins, both in the mammal's tissue and in the aminated ECM component. Furthermore, if TDP-PC includes a component having amine moieties, the polymeric component can covalently bind with them as well.

Binding between the polymeric component and the aminated ECM component (AECMC) serves to cross-link TDP-PC units (at least under conditions in which TDP-PC is condensed about and entangled with the polymeric component). Binding between the polymeric component and one or more tissues of the mammal serves to anchor the matrix at the body location at which it is applied or injected.

Examples of suitable polymeric components include chondroitins (e.g., chondroitin sulfate, CS), gelatins, keratins, hyaluronates, alginates, celluloses, guar and other gums, and dextrins. Compositions and methods for modifying each of these (and other) polymeric components to render them capable of covalently binding amine moieties are known to skilled artisans in this field.

The Amine Component

The composition includes an amine component that is capable of forming a covalent bond with the polymeric component of ECM. The amine component can be a polyamine, so that multiple polymeric component units can be linked to the same polyamine. The amine component is preferably an aminated ECM component (AECMC), such as an extract of ECM isolated from a mammal or a purified ECM component such as gelatin (e.g., purified bovine gelatin).

The amine component reacts with functional groups of the polymeric component that do not form covalent linkages with moieties on the surface of the mammal receiving the composition. Such reactions "cap the ends" of such functional groups and prevent non-desired reactions between those functional groups and other chemical moieties. The biocompatibility of the matrix formed in the mammal is thereby enhanced.

Because the amine component can inactivate functional moieties on the polymeric component (either by cross-linking them or by simply end-capping the moieties), the timing of contact between the amine component and the polymeric component must be controlled. Such contact should be substantially prevented until the composition is administered to the mammal at the site at which matrix formation is desired. It can also be desirable for there to be a temporal lag between delivery of the composition to the site and release of the amine component within the site. All of these ends can be achieved by sequestering the amine component in a thermally-releasible fashion, in a diffusion-ally-limited fashion, in a encapsulating-material-dissolution-limited fashion, or otherwise.

In one embodiment, the amine component is encapsulated within a material (e.g., within a lipid vesicle) that substantially prevents contact between an aqueous solvent on the outside of the material and the amine component within the material. Such encapsulation can include dissolving the amine component within the material, enveloping the amine component with a layer of the material (e.g., as in a lipid vesicle), or a combination of these. The encapsulating material must exhibit a thermal property (e.g., a melting or dissolution temperature) whereby the encapsulated amine component is able to contact the aqueous solvent surrounding the encapsulating material as the temperature rises above a selected value.

The temperature at which the encapsulating material permits contact between the solvent and the amine component should be selected to complement the CST of the TD polymer. Release of the amine component should occur at about the same temperature as the CST. Such release can be at a lower temperature to enhance cross-linking of TDP-PC units prior to condensation of TD polymer, or it can be at a higher temperature to enhance condensation of TD polymer prior to cross-linking of the DTP-PC units. The temperature at which the encapsulating material changes its property should ordinarily be at least slightly lower than the body temperature of the mammal that will receive the composition (unless release of the amine component is intended to be delayed until application or generation of a temperature in excess of normal body temperature in the animal, such as by external heating of a mammalian body part or development of inflammation at the delivery site).

Lipid vesicles are a preferred structure for encapsulating the amine component. A skilled artisan is able to construct a wide variety of lipid vesicles that exhibit differential solubility and/or permeability in aqueous solvents.

Another preferred structure for encapsulating the amine component is polymeric microparticles.

The amine component can be sequestered within microparticles of a material that either dissolves relatively slowly over time or that permits diffusion of the amine component therefrom relatively slowly (i.e., sufficiently slowly that the lag between mixing the encapsulated amine component and delivery of the suspension to a mammal does not permit sufficient release of the amine component within the suspension that most or substantially all reactive moieties of the polymeric component are end-capped). A wide variety of polymeric materials are known for encapsulating materials, and substantially any such material that provides a sufficient release rate of the amine component can be used.

The materials used for encapsulating the amine component should be biocompatible.

Bioactive Agents

The composition described herein can include one or more bioactive agents in addition to the other components described in this disclosure. Such agents can include mammalian (or other) cells, pharmaceutical agents, imaging agents, other components of ECM, other hydrogels, and radionuclides. Substantially any structure or molecule that can be suspended or dissolved in the composition can thus be delivered to a mammalian body location. Compositions containing such agents have a wide variety of uses in therapy, diagnosis, imaging, drug delivery, and other fields that are understood by artisans in various fields.

In one embodiment, the bioactive agent is a cell that is admixed with the composition prior to delivery of the composition to a body location of a mammal. If formation of covalent bonds between the cells and TDP-PC units is undesirable, the cells can be treated with end-capping or other agents to block such bonding. Alternatively, if binding of cells to the matrix is desirable, the cells can be permitted to bind with TDP-PC units prior to injection.

Adipose derived stem cells are an example of cells which can suitably be included within the composition described herein. These cells hold considerable promise for tissue engineering of the musculoskeletal system, repair of fistulas, and intervertebral disc regeneration.

In another embodiment, the composition is used as a drug delivery composition. A drug (either in a form that will not covalently bind with TDP-PC units or in an encapsulated form to prevent such binding) is dissolved or suspended in the composition prior to delivery of the composition to the mammal. Upon formation of a hydrogel matrix as described herein, the matrix serves as a depot containing the drug. If the drug is soluble in a body fluid at the location, the drug can elute from the matrix over a period of time.

The composition can include any of a number of known agents for attracting cells of various types (e.g., immune system cells or fibroblasts) to or into the matrix formed at the body location to which the composition is delivered.

Intervertebral Disc Regeneration

Degeneration of the intervertebral disc is a major cause of low back pain. Current scaffold-based regeneration strategies for the disc are not clinically feasible without adhesion to surrounding tissue, since implant expulsion can occur during loading and movement. Scaffolds for disc repair should have the ability to form a substantial interface with surrounding disc tissue to eliminate the risk of dislocation. Currently used bioadhesive systems have limited biocompatibility and thus have not been investigated as platforms for cell-based tissue repair.

The compositions described herein can be used for this purpose. The composition can be delivered to or into a human or other animal vertebral disk to replace or supplement naturally-occurring materials in the disc.

Fistula Repair

A fistula is an abnormal connection between two structures in the body and is often repaired with bioadhesive polymers. The compositions described herein can be used for this purpose.

In addition, because the compositions described herein and the matrix formed therefrom can maintain cells in a viable state, they can be used to deliver cells to sites of fistula repairs. By way of example, adipose-derived stem cells can be delivered to the fistula. The cells can differentiate into a fibroblast phenotype, generating scar tissue that plugs the fistula after the polymer degrades.

Hernia Repair

A hernia is the protrusion of an organ or the fascia of an organ through the tissue that normally contains it. Herniae commonly develop in the abdomen, when a weakness in the abdominal wall evolves into a localized hole. Treatments for herniae involve placing a mesh under the defect. Covering the hernia mesh with a patient's own pluripotent cells would reduce complications from the surgery, such as scarring, inflammation, and adhesion formation (Dolce et al., 2010, Surg. Endoscopy 24:2687-2693). In addition, utilization of a bioadhesive polymer in hernia repair would reduce surgical operating times, costs, and patient discomfort. Thus, there is tremendous potential in this area for a bioadhesive polymer that can be combined with autologous stem or other cells. The compositions described herein can be used for these purposes, either or both as bioadhesives for anchoring the mesh or as a coating for the mesh. Cells can be included in either the adhesive or coating application.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

Synthesis and Characterization of PNIPAAm-CS Copolymers

PNIPAAm-CS copolymers were synthesized in our laboratory. Methacrylated chondroitin sulfate (mCS) was prepared by known techniques (Bryant et al., 2004, Macromolecules 37:6726-33) with methacrylic anhydride using molar ratios of methacrylic anhydride (MA) to CS of 25:1, 50:1, and 200:1, yielding a degree of substitution (DS) of the CS of 0.1, 0.2, and 0.5, respectively, as determined by $^1$H NMR. Redox polymerization of NIPAAm monomer in the presence of each of the three batches of methacrylated CS was then performed. The molar ratio of NIPAAm monomer units to mCS chains was varied between 600:1 and 4000:1. Reaction products were freeze-dried and ground into powder prior to further use. Powders were redissolved in phosphate buffered saline (PBS, pH7.4) to form 5 wt % solutions.

Figure 2:
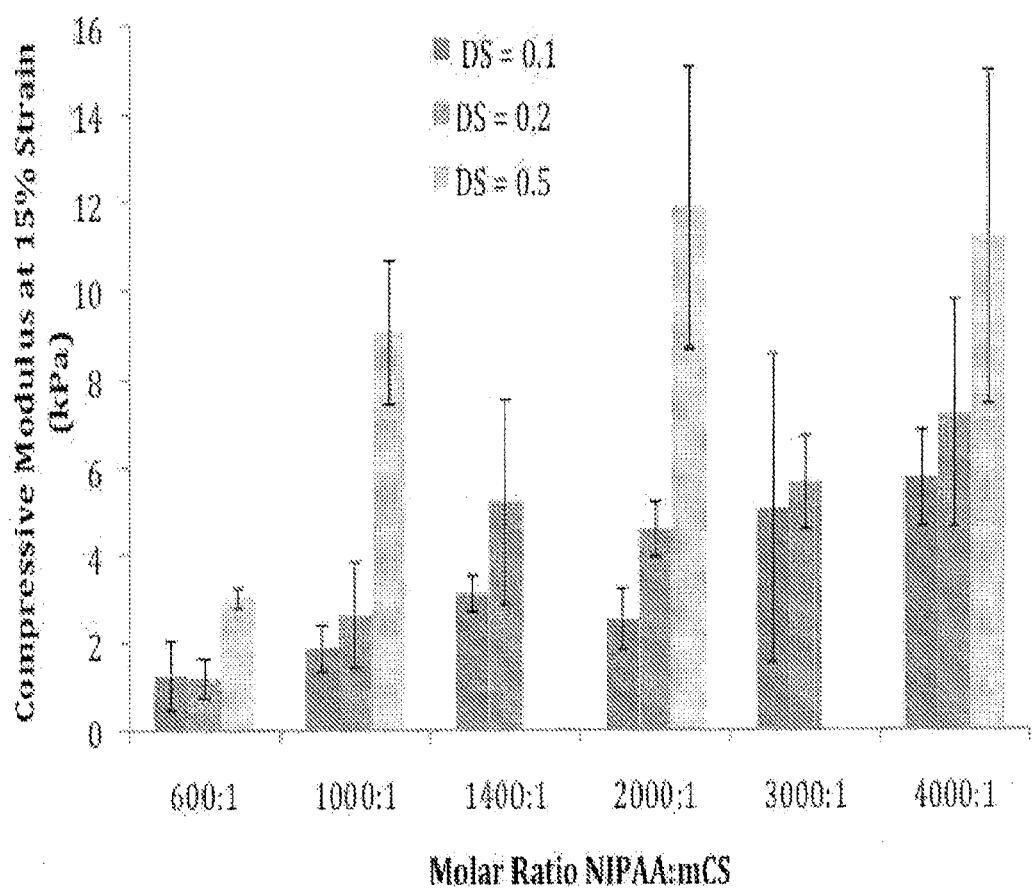
FIG. 2 is a bar graph comparing equilibrium compressive modulus values at 15% strain and 37° C. for hydrogel compositions described herein as a function of the molar ratio of NIPAAm:mCS and degree of substitution (DS) of mCS. The results shown here indicate that the hydrogels exhibited increasing modulus with increasing DS.

Compressive loading tests were performed using a FGS-200PV E-Force Test Stand device using standard methods. The biomaterial samples were equilibrated for 14 days at 37° C. in PBS prior to testing. Then, they were placed in a plexiglass bath containing a PBS bath at 37° C., mounted on the test machine. A flat platen fixture, fixed to the load cell, was used to compress the sample. E-force firmware was used on a personal computer to program the test displacement history and record force, deformation, and time data. Quasi-static testing was used to determine compressive mechanical behavior and moduli. For this condition, a rate of 100% strain/min was used until a maximum compression level of 30% was achieved. Compressive moduli at 15% strain is reported as the slope of the chord drawn between 10 and 20% strain and shown in FIG. 2. Results indicate that there were increasing trends in stiffness with increasing NIPAAm:CS molar ratio and degree of substitution of the CS.

Synthesis and Characterization of Aldehyde-Modified Chondroitin Sulfate

CS was oxidized using sodium periodate by known methods. Sodium periodate and CS were combined at a 1:1 weight ratio, dissolved in water, and reacted in the dark for 6 hours. The resulting product was purified by dialysis and aldehyde substitution was quantified with a hydroxylamine hydrochloride titration assay. Results indicated that 463 aldehyde moieties were formed per mole of CS.

Preparation and Characterization of Adhesive PNIPAAm-CS Copolymer

An adhesive polymer suspension was formulated by suspending in an aqueous buffer solution 4.6 wt % PNIPAAm-CS (the degree of substitution of the CS was 0.1, and the molar ratio of NIPAAm monomer to CS was 1000:1) and 2.8 wt % oxidized CS. Above the lower CST of PNIPAAm, a solidified gel-like material formed. While not being bound by any particular theory of operation, it was believed that the gel-like material resulted from desolubilization of NIPAAm polymer to form a collapsed network that physically entrapped oxidized CS chains within it, forming an interpenetrating hydrogel network.

Adhesive capacity of the solidified material was determined based on a modified test adapted from ASTM F 2258-05, Strength Properties of Adhesives in Tension. The testing was conducted using the FGS-200PV E-Force Test Stand. Rectangular sections of porcine tissue (area of approximately one square centimeter) was affixed to the upper and bottom fixtures of the mechanical testing system using cyanoacrylate adhesive. A thin layer of 100 microliters of hydrogel solution was uniformly spread between the tissue, the plates of the test fixture clamped together; and the gel was allowed to react with the tissue for approximately 5 minutes at 37° C. The specimens were tested to failure at a constant crosshead speed of 2 mm/min. The load versus distance was recorded. As controls, adhesion experiments were conducted with the skin in the absence of polymer, and with a PNIPAAm-CS polymer containing no oxidized CS.

Figure 3:
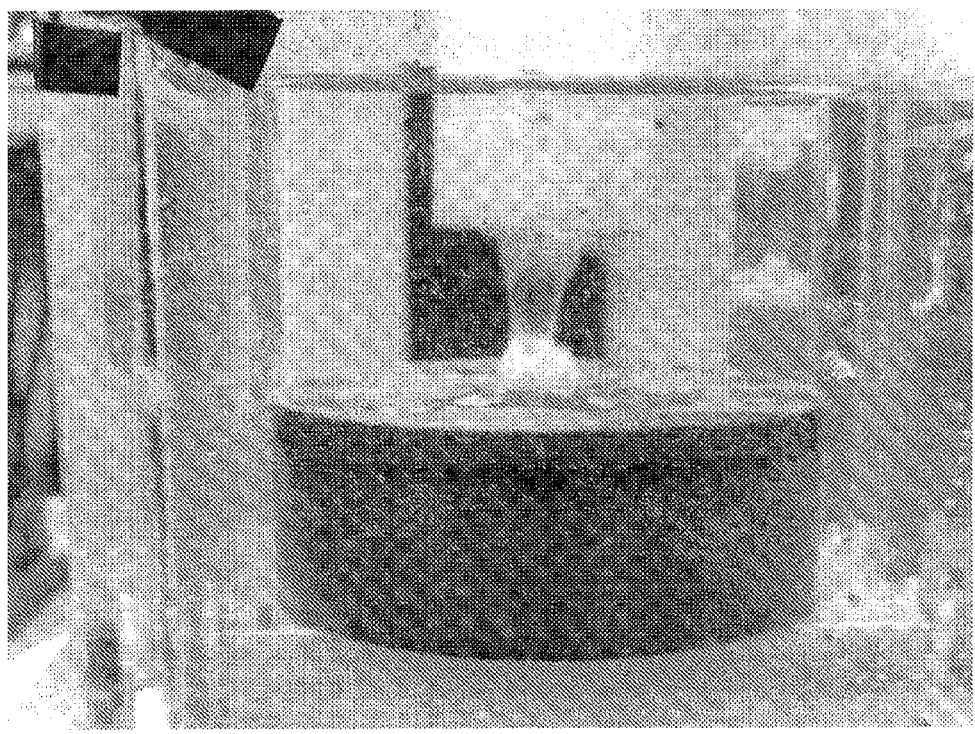
FIG. 3 is an image made during a bioadhesive force study described herein in which a PNIPAAm-CS copolymer including oxidized CS was used to adhere porcine skin to a substrate. Tensile force was applied to the copolymer, and the image shows stretching induced in the copolymer.

FIG. 3 depicts results of an adhesion experiment. As the upper fixture of the mechanical testing apparatus was withdrawn, the gel was stretched in the vertical direction, indicative of adhesion.

Figure 4:
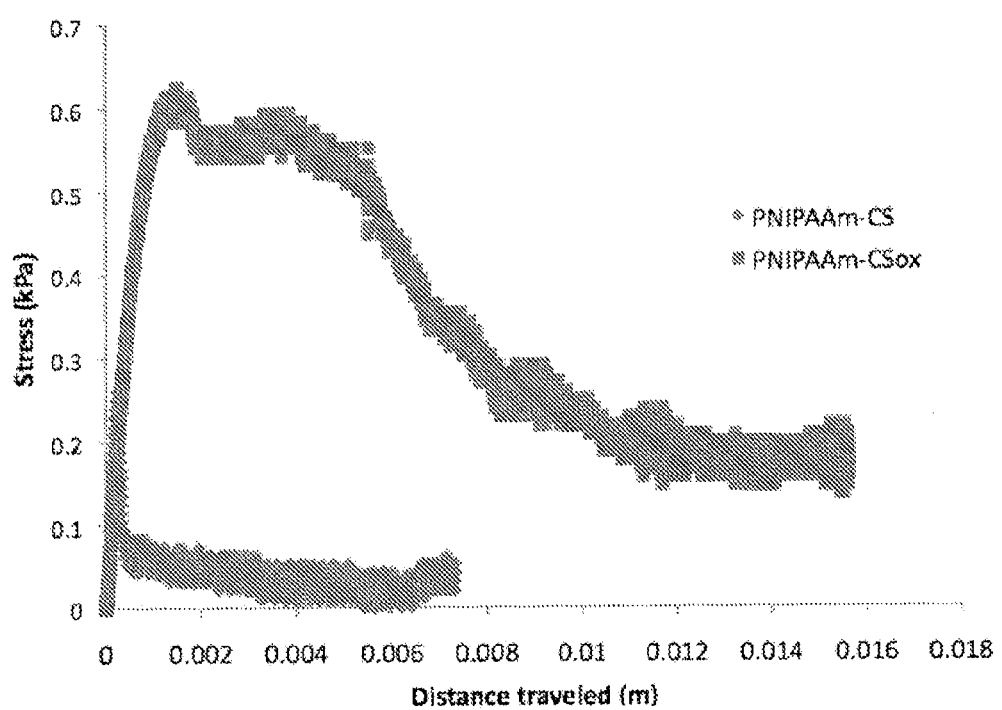
FIG. 4 is a pair of stress-strain curves for PNIPAAm-CS copolymer and the same copolymer in a composition that included oxidized CS (PNIPAAM-CSox). The copolymer including oxidized CS exhibited greater adhesion to the substrate.
Figure 5:
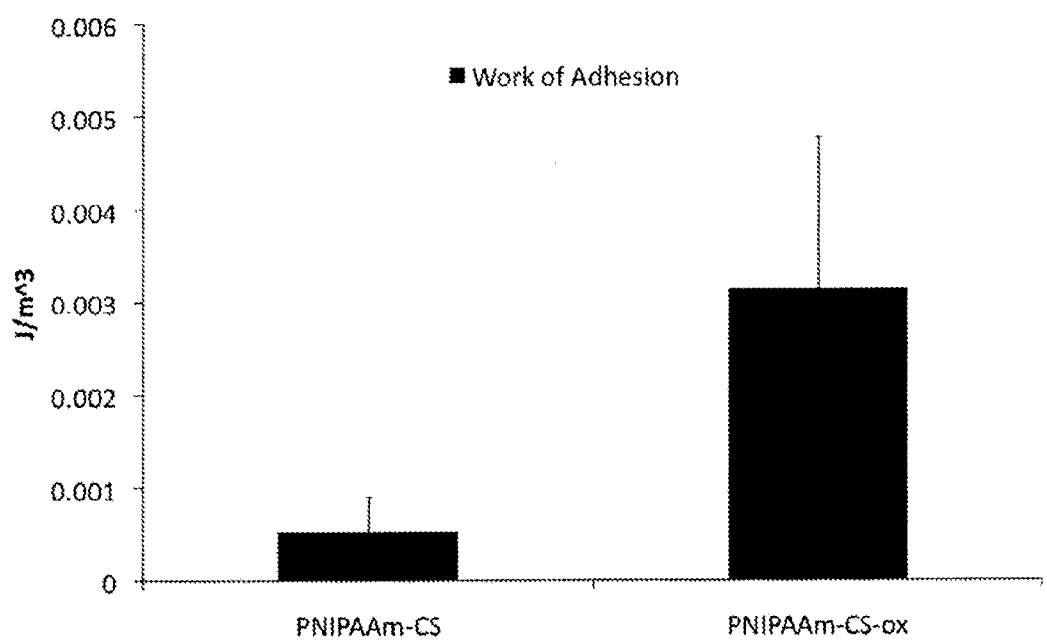
FIG. 5 is a bar graph that indicates the average (of six samples) work of adhesion for PNIPAAm-CS copolymer and for the same copolymer including oxidized CS (PNIPAAM-CSox). The copolymer including oxidized CS exhibited significantly higher work of adhesion, indicating greater adhesion to the substrate.
Figure 6:
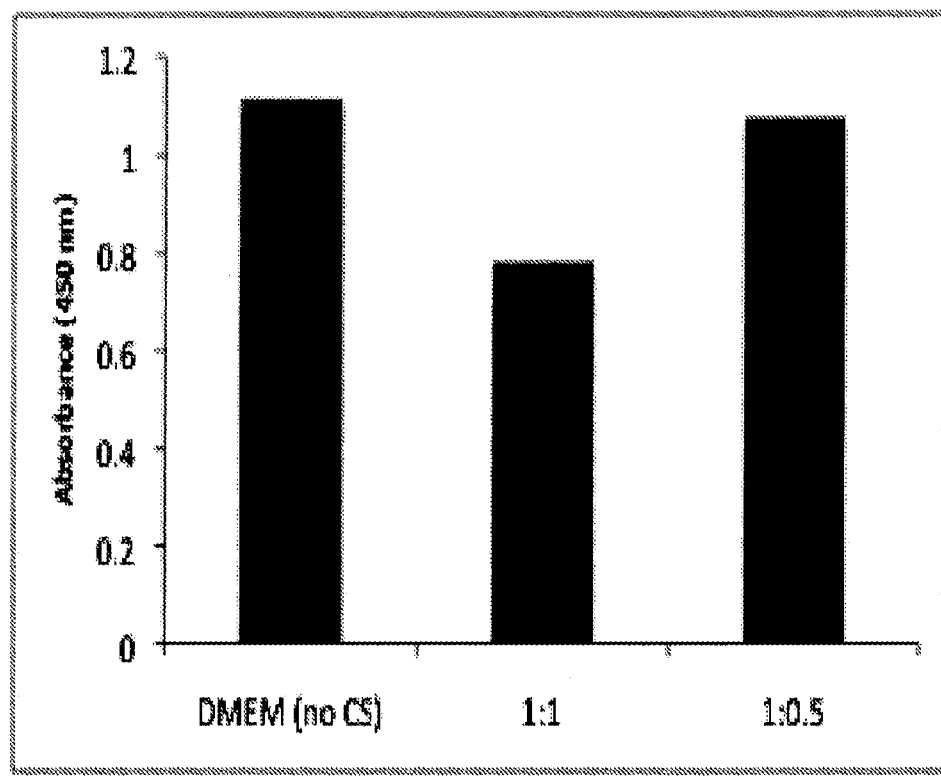
FIG. 6 is a bar graph that indicates XTT assay absorbance readings for adipose-derived stem cells (ASCs) exposed to DMEM medium containing no CS, in medium containing 3% (wt/vol) oxidized CS having a degree of aldehyde substitution of 1:1 (expressed as a weight ratio of CS:sodium periodate) or of 1:0.5, as described herein.

FIG. 4 depicts typical stress-strain curves for PNIPAAm-CS (lower data) and PNIPAAm-CS+oxidized CS (upper data). Movement of the upper fixture resulted in gradual increase in stress followed by a plateau region for both samples. This increase in load is indicative of adhesion to the substrate. However, the maximum stress for the sample containing oxidized CS was much higher, indicative of greater adherence to the substrate. The area under this curve, known as the work of adhesion, was calculated. The average values for six samples are shown in FIG. 5. Although adhesion occurred for both samples, the work of adhesion for the material including both PNIPAAm-CS and oxidized CS was significantly greater.

Cytocompatibility of the Adhesive Polymer

Cytocompatibility of oxidized CS alone was assessed. A 3% (wt/vol) solution of oxidized CS was prepared. Oxidized CS was synthesized using weight ratios of CS to sodium periodate of 1:1, 1:0.5, and 1:0.25 to produce varying degrees of aldehyde substitution. Each solution was added over confluent monolayers of adipose-derived stem cells. Controls included DMEM-F12 media containing no CS, as well as native CS. Cell viability over short-term exposure (less than 30 minutes) was assessed quantitatively with an XTT assay.

Results showed no significant trends toward loss of cell viability attributable to presence of the aldehyde groups for any of the formulations. These results indicate that the concentration of aldehyde groups in the hydrogels is low enough that it should not significantly affect cell survival in the short term. Viability of cells encapsulated in PNIPAAm-CS matrices containing oxidized CS can be evaluated over longer time periods. It is expected that the cells will experiences cytotoxicity due to the CS aldehyde. However, the inclusion of liposomes in the matrix, which are thermally triggered to release ECM components, is expected to support or enhance cellular survival over long time periods.

Example 2

Self-Assembling Biomimetic Hydrogels with Bioadhesive Properties for Tissue Engineering Applications Tissue engineering is a multidisciplinary field that aims to repair or regenerate lost or damaged tissues and organs in the body. Recent developments in this area have led to the design of biomimetic scaffolds, or three-dimensional engineered biomaterials that reproduce the mechanical and biochemical properties of natural tissue. Such materials have desirable biological properties and utilize cells and biochemical cues to promote the formation of new ECM. For the repair of certain load-bearing tissues such as bone and cartilage, success can be dependent on scaffold adhesion or integration with the surrounding host tissue to prevent dislocation. Such integration may be achieved with the use of a bioadhesive polymer that can covalently bond with tissue. However, current bioadhesive polymers suffer from poor biocompatibility. The objective of the experiments described in this example was to generate a bioadhesive polymer that, in addition to bonding with tissue, can support and cell survival post-adhesion.

In the work described in this example, a novel bioadhesive was developed combining PNIPAAm, CS, and gelatin-loaded liposomes in an injectable liquid composition. Gelatin is derived from ECM. The CS was modified with aldehyde groups ("CSaldehyde"), enabling it to form covalent bonds with primary amines in the surrounding tissues via a Schiff's base reaction, thereby making the polymer adhesive. The liposomes were designed to discharge gelatin at 37° C. after adhesion. This enhances the biocompatibility of the material by marking the assembly of a biomimetic matrix, and also covalently reacting with, or "end-capping", the cytotoxic aldehyde functionalities within the gel that did not participate in bonding with tissue upon contact.

Liposomes were prepared according to established methods (Burke et al., 2007, Biomed. Materials 2:203-210; Messersmith et al., 1998, Chem. Materials 10:117-124) using a blend of 1,2-bis(palmitoyl)-sn-glycero-3-phosphocholine (DPPC) and 1,2-bis(myristoyl)-sn-glycero-3-phosphocholine (DMPC), having a melting point of 37° C.

CS aldehyde was synthesized following a known procedure of sodium periodateoxidation (Kristiansen et al., 2010, Carbohyd. Res. 345:1264-1271; Wang et al., 2007, Nature Materials 6:385-392). PNIPAAm-CS copolymer was prepared as described elsewhere in this disclosure. Hydrogels, composed of PNIPAAm-CS, blended with 3 wt % CS aldehyde, were characterized.

Adhesion testing was performed using a Shimpo FGS-200PV E-Force Test Stand following the ASTM 2258 procedure for adhesives in tension (ASTM. Standard test method for strength properties of tissue adhesives in tension. ASTM International. 2005; F 2258-05:1308-12).

Cell viability was assessed using type 293 human embryonic kidney (293 HEK) cells and the reagents and instructions provided with the XTT-based toxicology assay kit (Sigma-Aldrich).

Lipid films composed of 90% DPPC and 10% DMPC were combined with a suspension of 2 mg/ml of gelatin in phosphate buffered solution (PBS) and extruded to form 0.2 µm diameter liposome vesicles. Release of gelatin at 37° C. due to the melting of the lipid bilayer was confirmed by BCA protein assay according to the supplier's directions (Pierce). The liposomes were shown to release 0.5 mg of gelatin per milliliter of liposome suspension when the liposomes were contacted with an aqueous fluid at 37° C. Negligible amounts of gelatin were released at 4° C.

Evidence of adhesion of the bioadhesive to porcine tissue was observed as visible stretching of the bioadhesive material during tensile property testing as described elsewhere in this disclosure.

Samples of the hydrogel bioadhesive material were subjected to tensile strength testing as described elsewhere in this disclosure. The material containing no liposomes exhibited a tensile strength of 702±311 Pa. Incorporation of gelatin-loaded liposomes within the material resulted in a decrease of the average tensile strength to 558±219 Pascals. Viability of cells subjected to the materials was about 3.6-fold greater for the material including the liposome-encapsulated gelatin than for the material lacking the liposomes when viability was assessed 24 hours after 293 HEK cells were encapsulated in the materials.

Several conclusions can be drawn from the information gleaned from the experiments described in this example. Biomimetic hydrogels composed of PNIPAAm-CS, CS aldehyde, and gelatin-loaded liposomes demonstrate bioadhesive properties. Addition of gelatin-loaded liposomes increased the biocompatibility while slightly decreasing adhesive strength. It can be expected that varying the concentration of CS aldehyde in the material can increase adhesive strength while maintaining biocompatibility of the bioadhesive materials.

Example 3

Characterization of Injectable Hydrogels Based on Poly (N-Isopropylacrylamide)-g-Chondroitin Sulfate with Adhesive Properties for Nucleus Pulposus Tissue Engineering The goal of the experiments described in this example was to develop an injectable tissue engineering scaffold for the treatment of lower back pain, which is caused by the dehydration of the nucleus pulposus (NP) of the intervertebral disc. Ideally, scaffolds for NP regeneration should have the ability to be implanted minimally invasively, form an adhesive interface with surrounding disc tissue to eliminate the risk of dislocation, and possess tunable mechanical properties for the maximum restoration of healthy disc biomechanics. In this work, a family of in situ forming hydrogels based on poly(N-isopropylacrylamide)-graft-chondroitin sulfate (PNIPAAm-g-CS) were evaluated for their compressive mechanical, degradation, and bioadhesive properties.

It was shown experimentally and computationally with the Neo-hookian hyperelastic model that increasing the crosslink density and decreasing the CS concentration in the copolymers generated hydrogels at 37° C. with increasing mechanical properties. The unconfirmed ompressive moduli ranged between 1.2 and 11.9 kPa at 15% strain, with several of the formulations in the same range as values reported for the native nucleus puposus. The family of hydro gels also exhibited degradability in the presence of chondroitinase ABC enzyme. Finally, the adhesive tensile strength of PNIP-AAm increased significantly with CS incorporation, ranging from 0.4 to 1 kPa after 5 mins of contact with porcine skin at 37° C. Results also indicate that solution viscosity, rather than crosslink density and CS concentration, may affect the adhesive properties. Taken together, these data indicate the potential of PNIP AAm-g-CS to function as a tissue engineering scaffold for the NP.

Introduction

Lower back pain is one of the most common medical problems in the world, affecting between 70% and 85% of the US population at some point during their lives. The intervertebral disc is composed of three basic structures: a central nucleus pulposus, a peripheral annulus fibrosus (AF), and two layers of cartilage covering the top and bottom called vertebral endplates. The main components of the disc are water, proteoglycans, and collagen. The primary function of the NP is to provide a bracing mechanism for the annulus under sustained loads. Vertical loads are transferred to the annulus from the nucleus in circumferential tension, preventing the fibers from buckling under sustained loads. One of the major causes of lower back pain is intervertebral disc degeneration, which is caused by a decline in the viable cell population of the disc and the rate of matrix synthesis. The decline of the cell population is thought to arise from calcification of the cartilaginous endplates inhibiting diffusion of nutrients to the disc. Specifically, this results in decreased proteoglycan content of the NP and thus its dehydration. After repeated physiological loading, tears, cracks and fissures in the annular tissues may form. Subsequently, back pain can develop as a result of nucleus tissue migrating through the annulus and impinging on nerve roots.

Recently, investigators have begun to focus on treatment strategies consisting of NP replacement combined with a tissue engineering strategy. In fact, studies in the field of regenerative medicine have shown that by introducing suitable, viable cells into the intervertebral disc, it is possible to produce new ECM components characteristic of the NP. The appropriate use of a scaffold has been shown to be a key determinant in the success of a cell-based therapy for IVD degeneration. NP cells have been shown to only retain their phenotype in a 3-dimensional environment. A polymeric biomaterial, in which cells can be uniformly distributed, can provide such conditions and also serve as nucleus replacement during the regeneration process. Several cell-seeded scaffolds have been investigated for this application, such as those based on PLGA, PLLA, and polycaprolactone (Zhang et al., 2008, Proceedings of the NASS 23rd Annual Meeting: The Spine Journal, pp. IS-191S; Richardson et al., 2006, Biomaterials 27:4069-78; Wan et al., 2008, Biomaterials 29:643-52). However, it is difficult to uniformly seed cells throughout these pre-formed matrices and implantation would be invasive.

There have also been investigations on injectable scaffolds for IVD tissue engineering. Many studies have focused on chitosan-glycerophosphate and collagen. While these natural polymers exhibit good biocompatibility and are permissive t.9ward cell attachment and differentiation, there is limited control over degradation rates and mechanical properties. Moreover, the adhesive properties of these scaffolds were not studied. To be clinically feasible for use during the later stages of annular degeneration, it is necessary to impart bioadhesive properties to the NP replacement in order to stabilize it in the center of the disc, since implant expulsion through the damaged annulus can occur during loading and movement. Thus, next generation scaffolds for disc repair should have the ability to form an interface with surrounding disc tissue to eliminate the risk of dislocation.

In the work described in this example, we addressed these needs by the development of a novel hydrogel partially composed of the thermally sensitive polymer poly(N-isopropylacrylamide) (PNIPAAm). Below its lower critical solution temperature (LCST) at 32° C., the polymer forms a miscible solution with water. Above the LCST, it becomes hydrophobic, so the polymer and water separate, forming a compact gel. Therefore, aqueous solutions of PNIPAAm can be implanted minimally invasively through a small gauge needle and solidify in situ without the use of toxic monomers or crosslinkers. For this reason, PNIPAAm has been extensively investigated for biomedical applications, such as pulsatile drug release, micellar delivery, and tissue engineering (Brazel et al. 1996, J. Controlled Release 36:57-64; Liu et al., 2005, Biomaterials 26:5064-74; Li et al., 2006, Polymer Doi:10.101/j.polymer.2006.04.041; Kim et al., 2003, Reactive & Functional Polymers 55:61-7; Kim et al., 2003, Biomacromolecules 4:1214-23). Previously, we investigated hydro gels based on PNIPAAm lightly crosslinked by difunctional poly(ethylene glycol) (PEG) for NP replacement and repair of spinal cord injury (Vernengo et al., 2008, J. Biomed. Mat. Res 84B:64-9; Conova et al., 2011, J. Neurosurg. Spine DOI: 10.3171/2011.7.SPINE11194). The incorporation of hydrophilic PEG chains enhanced the water content and elasticity of the hydrophobic PNIPAAm matrix at physiological temperature. The hydrogels were also shown to have mechanical properties in a suitable range for restoring the compressive stiffness of a denucleated intervertebral disc. Later, it was shown that, in a rodent model of spinal cord injury, the PNIPAAm-g-PEG copolymers did not illicit a greater inflammatory response than a collagen scaffold and supported graft cell survival (Comolli et al., 2009, Acta Biomater. 5:1046-55). We also demonstrated that PNIPAAm-g-PEG copolymers alone do not possess bioadhesive properties, but these could be imparted by incorporating polyethylene imine into the hydro gels and crosslinking to tissue with glutaraldehyde (Vernengo et al, 2010, J. Biomed. Mat. Res. 93B:309-17). However, PEI and glutaraldehyde are both potentially cytotoxic. PNIPAAm-PEG copolymers were also shown to be non-degradable, making the formulation non-ideal for tissue engineering applications.

In the work described in this Example, we investigated grafting PNIPAAm with the natural biopolymer CS in order to overcome the shortcomings of the previously investigated formulation. Chondroitin sulfate (CS), an ECM component of the native IVD tissue, was incorporated into the PNIPAAm matrix to form a semi-synthetic injectable hydrogel. We hypothesized that with this system it would be possible to retain the favorable mechanical characteristics of PNIPAAm and the enzymatic degradability, anti-inflammatory activity, water and nutrient absorption of CS. In addition, CS is a polysaccharide generally known to be mucoadhesive due to the presence of hydroxyl groups, thus we hypothesized that it would impart increased bioadhesive characteristics to injectable hydrogels based on PNIPAAm.

Other investigators have studied systems based on PNIPAAm covalently linked to natural biopolymers. For instance, Gupta et al. studied a copolymer with carboxymethyl guar as an industrial thickener (Gupta et al., 2011, Carbohydrate Polymers 83:74-80). Another group studied the rheological properties of alginate grafted with PNIPAAm, and chitosan-g-PNIPAAm nanogels were investigated for drug delivery (Vasile et al. 2011, Carbohydrate Polymers 86:77-84; Duana et al., 2011, Int. J. Pharmaceutics 409:252-9). Yet, none of these applications required the formation of a structural gel above the LCST. Hydrogels composed of PNIPAAm and CS were prepared for use as a biomimetic actuator (Varghese et al., 2008, Sensors and Actuators B 135:336-41). The highly crosslinked system was not in situ forming, thus exhibited only a change in volume due to the LCST of the PNIPAAm. Furthermore, the bioadhesive properties of these systems have not been investigated.

In the work described in this example, PNIPAAm copolymers with CS were prepared by polymerizing the monomer NIPAAm in the presence of methacrylate-functionalized CS. Because the in situ forming qualities of PNIPAAm are retained, the materials are referred to in this work as grafted copolymers, to distinguish them from highly crosslinked systems. Here, we analyze the swelling, mechanical, degradation, and adhesive properties of the family of injectable PNIPAAm-g-CS copolymers in order to evaluate their potential to function as tissue engineering scaffolds for NP regeneration.

Materials

Chondroitin sulfate, chondroitinase ABC, and methacrylic anhydride were all purchased from Sigma Aldrich and used as received. N-isopropylacrylamide (NIPAAm) monomer (Sigma-Aldrich) was re-crystallized in n-hexane before use. All solvents were of analytical grade. Fresh porcine skin was obtained from a butcher.

Methods

Graft Copolymer Synthesis

Methacrylated chondroitin sulfate (mCS) was prepared with methacrylic anhydride (MA) using a procedure developed by Bryant et. al. (2004, Macromolecules 37:6726-33). The molar ratios of MA to CS used were 25:1, 50:1, and 200:1, producing a degree of substitution (DS) of the CS of 0.1, 0.2, and 0.5, respectively, as determined by 1H NMR with D20 as solvent as described (Wang et al., 2003, Carbohydrate Polymers 52:389-96). Redox polymerization of NIPAAm monomer in the presence of each of the three batches of methacrylated CS was then performed. The molar ratio of NIPAAm monomer units to mCS chains used in the reaction mixture was varied between 600:1 and 4000:1. Grafting of CS onto PNIPAAm was verified also with 1H NMR by the absence of peaks for the vinyl resonances for the methacrylate protons on the CS at $\delta$=5.7 and 6.1 ppm and the presence of peaks for CS sugar backbone at 3-4.8 ppm and the isopropyl groups on the NIPAAm at 0.99 ppm (Ma et al., 2004, J. Colloid Interface Sci. 276:53-9). A PNIPAAm homopolymer was also prepared under identical reaction conditions but in the absence of mCS. The reaction products were freeze-dried, ground into a powder and re-dissolved in phosphate buffered saline (PBS, pH 7.4) to form aqueous solutions with a range of concentrations between 1 and 10 wt %. For these studies, gels formed from 5 wt % solutions were characterized, based on polymer ability to gel at the lowest solution viscosity at room temperature.

Gel Swelling

To characterize gel swelling, approximately 1 mL of each 5 wt % solution was placed in preweighed glass vials and heated to 37° C. to form a solid gel. The gels were then immersed in PBS at 37° C. and allowed to equilibrate for 14 days. Water content of the gels at 14 days immersion at 37° C. was calculated by determining the mass of water present per gram of dry polymer (Mwet/Mdry). This was compared to the water content of the aqueous solution at room temperature, prior to gelation. The percentage water loss was calculated by taking the ratio of these two quantities.

Percent loss In water content=100×[((Mwet/Mdry) evaluated at 37° C. after 14 days)/((Mwet/Mdry) evaluated at 25° C. after 0 days)]

Compressive Mechanical Properties

Cylindrical hydrogel samples were equilibrated for 14 days at 37° C. in PBS prior to testing. Then, they were placed in a plexiglass bath containing a PBS bath at 37° C., mounted on an FGS-200PV E-Force Test Stand. A flat platten fixture, which is fixed to the load cell, was used to compress the sample. E-force firmware was used on a PC to program the test displacement history and record force, deformation and time data. Quasi-static testing was used to determine compressive mechanical behavior and moduli. For this condition, a rate of 100% strain/min was used until a maximum compression level of 30% was achieved. Compressive modulus at 15% strain was reported as the slope of the chord drawn between 10 and 20% strain.

Neo-Hookean Modeling of Gel Mechanical Properties

A neo-Hookean strain-energy density function was used to describe nonlinear hyperelastic behavior of the hydrogels. Using a nonlinear least squares fit in MATLAB, this model was fit to the compression experimental data to determine a shear modulus for each of the material formulations.

Bioadhesive Force Studies

The tensile strength of the copolymers at 37° C. was tested based on a modified version of ASTM F 2258-05, Strength Properties of Adhesives in Tension (ASTM. Standard test method for strength properties of tissue adhesives in tension. ASTM International 2005; F 2258-05:1308-12). Sections porcine tissue were cut into one square centimeter pieces and affixed to the upper and bottom fixtures of a FGS-200PV E-Force Test Stand using cyanoacrylate adhesive and warmed to 37° C. A thin layer of hydrogel solution (200 microliters) was uniformly spread between the tissue, the surfaces opposed; and the gel allowed to contact the tissue at 37° C. for 5 minutes. The upper fixture was then withdrawn at a rate of 2 millimeters per minute and load-displacement data captured by a computer. The tensile strength of the samples was calculated by normalizing the maximum load to the bond area. Three different molar ratios of NIPAAM:mCS were tested (2000:1, 1000:1 and 600:1). For each molar ratio, the DS of the mCS in the reaction mixture was varied between 0.1 and 0.2. As a comparison, the tensile strength of the PNIPAAm homopolymer was also evaluated in parallel.

Hydrogel Degradation Characteristics

The degradation behavior of two PNIPAAm-CS hydrogels was investigated in the presence of the enzyme chondroitinase ABC. To prepare the gel samples, NIPAAm was polymerized in the presence of mCS (DS 0.5) in a molar ratio of NIPAAm monomer to mCS of 600:1 (high CS content) and 2000:1 (low CS content). To characterize degradation, approximately 0.5 mL of 5 wt % polymer solution was heated to 37° C. within a closed vial and the precipitated gels were immersed in 4 mL of chondroitinase ABC solution (0.0066 U/mL) and then kept in a shaking incubator at 37° C. The enzyme solutions were replaced daily to maintain maximum enzyme activity. At timed intervals, samples were retrieved, excess solution removed from the vials, and the samples dried completely. The mass retention of the gels at time t were calculated. Controls were also studied by soaking hydrogels in PBS containing no chondroitinase enzyme.

Results and Discussion

Despite the advantages of PNIPAAm having a phase transition between room and physiological temperature, allowing for injectability, a major limitation of the polymer has been its excessive syneresis above the LCST (Vernon et al., 2000, J. Biomed. Mat. Res. 51:69-79). This dehydration of the polymer chains could potentially result in cellular exclusion from the matrix and excessive volume loss. However, the fixed negative charges on chondroitin sulfate (—COO— and —$SO_3^-$) at neutral pH have been shown to enhance osmotic pressure of highly crosslinked PNIPAAm networks. Swelling data for our in situ forming system at 37° C. is consistent with these prior findings. The PNIPAAm homopolymer gel exhibited an approximate 83.0±3.6% water loss over the 14 day period. This was significantly higher ($p<0.05$) than all of the hydrogels containing CS, except for those prepared with a molar ratio of NIPAAm:mCS 4000:1 and a DS of the mCS equal to 0.5. Furthermore, the gels containing the most CS (NIPAAm:mCS 600:1) exhibited a significantly lower percentage water loss over the 14 day period ($p<0.05$) than all the other formulations, attributable to the high osmotic pressure of CS. Also, it was demonstrated that increasing the DS of the mCS produced increasing trends in water loss. The higher degree of methacrylate substitution likely increases the crosslink density of the network, allowing it to accommodate less water than gels with a looser crosslinked structure.

Experimental results for the compressive mechanical tests showed increasing trends in stiffness with increasing NIPAAm:CS molar ratio and DS of the mCS. Importantly, the modulus values for the gels with molar ratios of NIPAAm:mCS 4000:1 (DS 0.1, 0.2 and 0.5), NIPAAm:mCS 2000:1 (DS 0.2 and 0.5), and NIPAAm:mCS 1000:1 (DS 0.5) were in the same range as native nucleus pulposus tissue tested under unconfined compression, 5-6.7 kPa.

The mechanical properties were also investigated computationally using a neo-Hookean material model. The results indicate that the model is a good fit for our range of experimental data. The computed shear modulus increases as the molar ratio of NIPAAm:mCS increases for each of the degree of substitution of CS. Similarly, the shear modulus also increases for larger degree of substitution of CS. Overall, both the experimental and computational mechanical data results are in good agreement with the swelling data, which indicate that both these parameters cause decreasing trends in the water content of the gels. Water in hydrogels acts as a plasticizer, increasing flexibility of the polymer chains, decreasing the mechanical properties. It is important to note that in order to evaluate these materials for NP replacement and tissue engineering, further material characterization is necessary, such as fatigue and stress relaxation. Ideally, the mechanical behavior of the scaffold should mimic the properties of the native NP, lowering the risk that transplanted cells will be exposed to abnormal biomechanical loads.

Qualitative evidence of adhesion was seen, with the hydrogel being stretched in the vertical direction as the upper fixture was withdrawn. Quantitatively, all of the polymer formulations containing CS exhibited increasing trends in tensile strength compared to the homopolymer. These results make sense, since CS is known to be mucoadhesive. Adhesion results from ionic and/or hydrogel bonding between the CS in the hydrogels and matrix components, such as proteoglycan, in the porcine tissue. Interestingly, for the CS concentration range studied, increasing the amount of CS in the hydrogels did not produce significant increases in adhesive tensile strength.

For the hydrogels prepared with molar rations of NIPAAm:mCS of 2000:1 and 1000:1, varying the DS of the mCS did not produce a consistent effect on the adhesive tensile strength. However, it is important to note that a significant decrease in tensile strength occurred for the 600:1 NIPAAm:mCS copolymer when the DS of the mCS was increased from 0.1 to 0.2. This was also observable during testing. The authors attribute this phenomenon to the high viscosity of this formulation at room temperature. While the other formulations formed flowable liquids in room temperature, the aqueous 5% copolymer solution of NIPAAm:mCS 600:1, DS 0.5 had the consistency of a semisolid, likely due to the high CS content and crosslink density. Prior work by other investigators has indicated that viscosity of an in situ formed gel affects its ability to penetrate the texture of the tissue surface. This penetration causes mechanical interlocking to occur, which enhances the adhesion of the two pieces of sol tissue. While this sample does have higher adhesive tensile strength than the homopolymer, indicating that CS incorporation does in fact playa role in bioadhesion, the decrease in tensile strength compared to the low viscosity formulations indicates that the adhesive behavior of our system is at least in part attributable to mechanical interlocking with the texture of the porcine skin. It is important to note that, to our knowledge, there are no existing studies on the requisite adhesive characteristics to prevent expulsion of a hydrogel nucleus replacement. An advantage of making PNIPAAm copolymers with CS is that the carboxyl groups on the CS can be modified to form covalent bonds the tissue extracellular matrix, using functional groups such as N-hydroxysuccinimide or aldehydes, which will increase bioadhesive strength if necessary.

The degradation behavior of PNIPAAm-g-CS in the presence of chondroitinase ABC enzyme was studied. Both formulations exhibited approximately 20% loss in dry mass after 16 hours exposure to the chondroitinase ABC. At day 3, the high CS content gels (600:1 NIPAAm:mCS) exhibited significantly higher mass loss than the low CS content gels (2000:1). At day 7, the 600:1 NIPAAm:mCS gels exhibited complete degradation and the 2000:1 exhibited 27.2±0.6% mass loss. These values were significantly higher that the same gels soaked in PBS alone for 14 days (36.1±2.9 and 23.4±0.4%, for 600:1 and 2000:1, respectively). Mass loss observed in PBS alone may be attributed to slow dissolution of unbound CS from the gels, yet dissolution is clearly enhanced by its enzymatic cleavage. It is also important to note that only samples prepared with a DS of the CS equal to 0.5 were characterized in this study. Bryant et al. found that varying the degree of methacrylation of CS, and thus the crosslink density of hydro gels, did not affect susceptibility of the CS to enzymatic degradation. Thus, it is reasonable to assume that 600:1 and 2000:1 PNIPAAm-g-CS hydrogels prepared with lower crosslink densities will also exhibit mass loss in the presence of ChABC. Taken together, the results indicate that variation of the overall CS content allows for control over the extent of degradation of the gels.

CONCLUSIONS

In the work described in this Example, a family of novel injectable PNIPAAm-g-CS hydrogels were evaluated for their swelling, mechanical, degradation, and adhesive characteristics. It was found that varying the degree of methacrylate substitution of the CS and the overall CS content in the hydro gels allowed for control over the resulting properties of the hydrogels. Overall, increasing the CS content minimized the water loss of the hydrogels over a 14 day period in vitro, compared to a homopolymer control. Incorporation of CS significantly increased the adhesive strength of PNIPAAm hydrogel after 5 mins of contact with porcine skin at 37° C. The average adhesive tensile strength of PNIPAAm-g-CS adhesive varied between 0.4 and 1 kPa, though no significant changes were seen with CS content in the concentration range studied. Lower solution viscosity at room temperature was also found to produce more favorable adhesion characteristics, indicating that mechanical interlocking between the porcine skin and the in situ formed hydrogel may also play a role in bioadhesion. Degradation in the presence of chondroitinase ABC enzyme was shown, with gels containing higher concentrations of CS exhibiting more mass loss over a 7 day period in vitro. Increasing the degree of methacrylate substitution of the CS was found to cause increasing trends in water loss, compressive stiffness, and computed shear modulus of the gels. The hydrogels exhibited compressive modulus values at 15% strain between 1.2 and 11.9 kPa, similar in magnitude to what has been reported for the native nucleus pulposus.

These studies indicate the potential of the PNIPAAm-g-CS system to function as a tunable tissue engineering scaffold for the NP of the intervertebral disc.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

The invention claimed is:

1. A method for intervertebral disc regeneration, comprising delivering to or into a human or other mammalian vertebral disc in vivo, a liquid composition comprising an aqueous solvent having suspended therein:
   a) a biocompatible thermally-desolubilizable (TD) polymer that exists in an extended form below a critical solution temperature (CST) that is lower than the normal body temperature of the mammal and in a condensed form at or above the CST;
   b) an aminated component of a mammalian extracellular matrix (ECM), in a releasable encapsulated form, wherein the aminated component is releasable from the encapsulated form within the body of the mammal; and
   c) a polymeric component of a mammalian ECM, the polymeric component bearing functional moieties capable of forming covalent bonds with amine moieties,
   whereby when the composition is delivered to the vertebral disc, the polymer is transformed from its extended form to its condensed form, the aminated component is released from its encapsulated form, and the polymeric component binds with the aminated component, thereby forming a disc-replacing or disc-supplementing matrix.

2. The method of claim 1, wherein said delivering is to a human disc in vivo.

3. The method of claim 1, wherein the TD polymer is selected from the group consisting of poly(ethylene oxides) (PEOs), poly(propylene oxides) (PPOs), copolymers of PEO and poly(lactic acid) (PLA), poly(n-isopropyl acrylamides) (PNIPAAms), mixtures of the foregoing, and copolymers of the foregoing.

4. The method of claim 1, wherein the TD polymer is covalently linked with an ECM polymer.

5. The method of claim 4, wherein the ECM polymer is the same polymer as the polymeric component.

6. A method for fistula repair, comprising delivering to a fistula in a human or other mammal, a liquid composition comprising an aqueous solvent having suspended therein:
   a) a biocompatible thermally-desolubilizable polymer (TD) that exists in an extended form below a critical solution temperature (CST) that is lower than the normal body temperature of the mammal and in a condensed form at or above the CST;
   b) an aminated component of a mammalian extracellular matrix (ECM), in a releasable encapsulated form, wherein the aminated component is releasable from the encapsulated form within the body of the mammal; and
   c) a polymeric component of a mammalian ECM, the polymeric component bearing functional moieties capable of forming covalent bonds with amine moieties,
   whereby when the composition is delivered to the fistula, the polymer is transformed from its extended form to its condensed form, the aminated component is released from its encapsulated form, and the polymeric component binds with the aminated component, thereby forming a bioadhesive matrix, repairing the fistula.

7. The method of claim 6, wherein said composition further comprises:
   d) cells of the same species as the mammal suspended in the solvent.

8. The method of claim 7, wherein said cells comprise adipose-derived stem cells.

9. The method of claim 8, wherein said adipose-derived stem cells differentiate into a fibroblast phenotype, generating scar tissue that plugs the fistula after the polymer degrades.

10. The method of claim 8, wherein said delivering is to a human.

11. The method of claim 8, wherein the TD polymer is selected from the group consisting of poly(ethylene oxides) (PEOs), poly(propylene oxides) (PPOs), copolymers of PEO and poly(lactic acid) (PLA), poly(n-isopropyl acrylamides) (PNIPAAms), mixtures of the foregoing, and copolymers of the foregoing.

12. The method of claim 8, wherein the TD polymer is covalently linked with an ECM polymer.

13. The method of claim 12, wherein the ECM polymer is the same polymer as the polymeric component.

14. A method for hernia repair, comprising
   1) covering a localized hole in the abdominal wall of a human or other mammalian patient with mesh, and
   2) covering the mesh with a liquid composition comprising an aqueous solvent having suspended therein:
      a) a biocompatible thermally-desolubilizable polymer (TD) that exists in an extended form below a critical solution temperature (CST) that is lower than the normal body temperature of the mammal and in a condensed form at or above the CST;
      b) an aminated component of a mammalian extracellular matrix (ECM), in a releasable encapsulated form, wherein the aminated component is releasable from the encapsulated form within the body of the mammal; and
      c) a polymeric component of a mammalian ECM, the polymeric component bearing functional moieties capable of forming covalent bonds with amine moieties,
      whereby when the composition is delivered to the mesh in vivo, the polymer is transformed from its extended form to its condensed form, the aminated component is released from its encapsulated form, and the polymeric component binds with the aminated component, thereby forming a bioadhesive matrix, repairing the hernia.

15. The method of claim 14, wherein said composition further comprises pluripotent cells from said patient, suspended in the solvent.

16. The method of claim 15, wherein said delivering is to a human patient.

17. The method of claim 15, wherein the TD polymer is selected from the group consisting of poly(ethylene oxides) (PEOs), poly(propylene oxides) (PPOs), copolymers of PEO and poly(lactic acid) (PLA), poly(n-isopropyl acrylamides) (PNIPAAms), mixtures of the foregoing, and copolymers of the foregoing.

18. The method of claim 15, wherein the TD polymer is covalently linked with an ECM polymer.

19. The method of claim 18, wherein the ECM polymer is the same polymer as the polymeric component.

* * * * *